(12) United States Patent
Murata (10) Patent No.: US 9,523,655 B2
(45) Date of Patent: Dec. 20, 2016

(54) GAS CONCENTRATION DETECTOR

(71) Applicant: DENSO CORPORATION, Kariya, Aichi-pref. (JP)

(72) Inventor: Yu Murata, Obu (JP)

(73) Assignee: DENSO CORPORATION, Kariya (JP)

( * ) Notice: Subject to any disclaimer, the term of this patent is extended or adjusted under 35 U.S.C. 154(b) by 28 days.

(21) Appl. No.: 14/495,668

(22) Filed: Sep. 24, 2014

(65) Prior Publication Data

US 2015/0083588 A1 Mar. 26, 2015

(30) Foreign Application Priority Data

Sep. 24, 2013 (JP) ................................. 2013-197114

(51) Int. Cl.
*G01N 27/41* (2006.01)
*G01N 27/416* (2006.01)

(52) U.S. Cl.
CPC .......... *G01N 27/4163* (2013.01); *G01N 27/41* (2013.01)

(58) Field of Classification Search
CPC ................ G01N 27/4163; G01N 27/41; G01N 27/404–27/407; G01N 27/409; G01N 27/419; G01N 1/2252; G01M 15/10; G01M 15/102; G01M 15/104
See application file for complete search history.

(56) References Cited

U.S. PATENT DOCUMENTS

| 6,996,499 B2 | 2/2006 | Kurokawa et al. |
| 2004/0153258 A1 | 8/2004 | Kurokawa et al. |

FOREIGN PATENT DOCUMENTS

| JP | 4020019 | 10/2007 |
| JP | 2011-58834 | 3/2011 |
| JP | 2015-62013 | 4/2015 |

*Primary Examiner* — Gurpreet Kaur
(74) *Attorney, Agent, or Firm* — Nixon & Vanderhye PC (57) ABSTRACT

A gas concentration detector includes a gas sensor and an abnormality detecting section. The gas sensor includes a single solid electrolyte body having oxygen ion conductivity and electrodes formed on both surfaces of the single solid electrolyte body. The abnormality detecting section is configured to apply an AC voltage to a specific one of the electrodes and concurrently measure currents flowing respectively between the specific electrode and each of the other electrodes through the solid electrolyte body, and determine that at least one of wires respectively connected to the corresponding electrodes is broken if at least one of the measured currents is smaller than a predetermined value.

3 Claims, 9 Drawing Sheets

GAS CONCENTRATION DETECTOR

This application claims priority to Japanese Patent Application No. 2013-197114 filed on Sep. 24, 2013, the entire contents of which are hereby incorporated by reference.

BACKGROUND OF THE INVENTION

1. Field of the Invention

The present invention relates to a gas concentration detector including a gas sensor and an abnormality detecting section for detecting abnormality in the gas sensor.

2. Description of Related Art

There is known a gas concentration detector for detecting concentration of NOx contained in exhaust gas of an automobile, for example, the gas concentration detector including a gas sensor and an abnormality detecting section for detecting abnormality in the gas sensor. For example, refer to Japanese Patent No. 4020019.

The gas sensor of this gas concentration detector includes two plate-like solid electrolyte bodies having oxygen ion conductivity. Each solid electrolyte body is formed with electrode on both surfaces thereof. Cells are formed by the solid electrolyte bodies and the electrodes. The cells include a pump cell for adjusting an oxygen concentration in a measurement gas, a monitor cell for detecting the oxygen concentration in the measurement gas and a sensor cell for detecting concentration of a specific gas contained in the measurement gas. This gas concentration detector is configured to measure a current flowing to the monitor cell and a current flowing to the sensor cell, and calculate the concentration of the specific gas based on the measured values of theses currents.

The electrodes are connected with wires through which the currents flow. Therefore, if any one of the wires breaks for some reason, it becomes impossible to accurately measure the concentration of the specific gas. Accordingly, the gas concentration detector has to periodically check whether there is breakage in any one of the wires.

To check wire breakage, an AC voltage is applied to each of the cells through the wires. As explained in the foregoing, each cell has the structure as a capacitor in which electrodes are formed on both surfaces of a solid electrolyte body. Accordingly, if there is no wire breakage, an AC current flows to the cell when the AC voltage is applied to the cell, while on the other hand, if there is wire breakage, no AC current flows to the cell even when the AC voltage is applied to the cell. Hence, by detecting whether the value of the AC current flowing to the cell when the AC voltage is applied to the cell is larger then a predetermined threshold value or not, it is possible to determine presence or absence of wire breakage.

However, in the above gas concentration detector, the cell formed in one of the two solid electrolyte bodies is electrically insulated from the cell formed in the other solid electrolyte body. Therefore, to determine presence or absence of wire breakage for all the wires, it is necessary to apply the AC voltage to each of the cells individually. Accordingly, since a circuit for applying the AC voltage has to be provided for each of the cells, the circuit scale and cost of the abnormality detecting section increase. In addition, since the AC voltage is applied to the cells successively, it takes time to complete the wire breakage check.

SUMMARY

An exemplary embodiment provides a gas concentration detector comprising a gas sensor and an abnormality detecting section connected to the gas sensor for detecting abnormality in the gas sensor, wherein the gas sensor includes a solid electrolyte body having oxygen ion conductivity, electrodes formed on both surfaces of the solid electrolyte body, and wires respectively connected to the electrodes, the electrodes include a pump electrode, a monitor electrode and a sensor electrode which are formed on one of the surfaces of the solid electrolyte body so as to be exposed to a measurement gas, and a reference electrode formed on the other surface of the solid electrolyte body so as to be exposed to a reference gas, the solid electrolyte body, the pump electrode and the reference electrode form a pump cell for adjusting an oxygen concentration of the measurement gas, the solid electrolyte body, the monitor electrode and the reference electrode form a monitor cell for detecting the oxygen concentration of the measurement gas, the solid electrolyte body, the sensor electrode and the reference electrode form a sensor cell for detecting a concentration of a specific gas contained in the measurement gas, the pump electrode, the monitor electrode, the sensor electrode and the reference electrode are formed in the single solid electrolyte body, each of the wires respectively connected to the pump electrode, the monitor electrode and the sensor electrode are connected with a current measuring section, the abnormality detecting section is configured to apply an AC voltage to a specific one of the pump electrode, the monitor electrode, the sensor electrode and the reference electrode, and concurrently measure currents flowing respectively between the specific electrode and each of the other of the pump electrode, the monitor electrode, the sensor electrode and the reference electrode through the solid electrolyte body using the current measuring sections, and the abnormality detecting section is configured to determine that at least one of the wires respectively connected to the pump electrode, the monitor electrode, the sensor electrode and the reference electrode is broken if at least one of the currents measured by the current measuring sections is smaller than a predetermined value.

According to the exemplary embodiment, there is provided a gas concentration detector whose abnormality detecting section is simple in structure and capable of determining whether there is a wire breakage in its gas sensor in a short time.

Other advantages and features of the invention will become apparent from the following description including the drawings and claims.

PREFERRED EMBODIMENTS OF THE INVENTION

Figure 1:
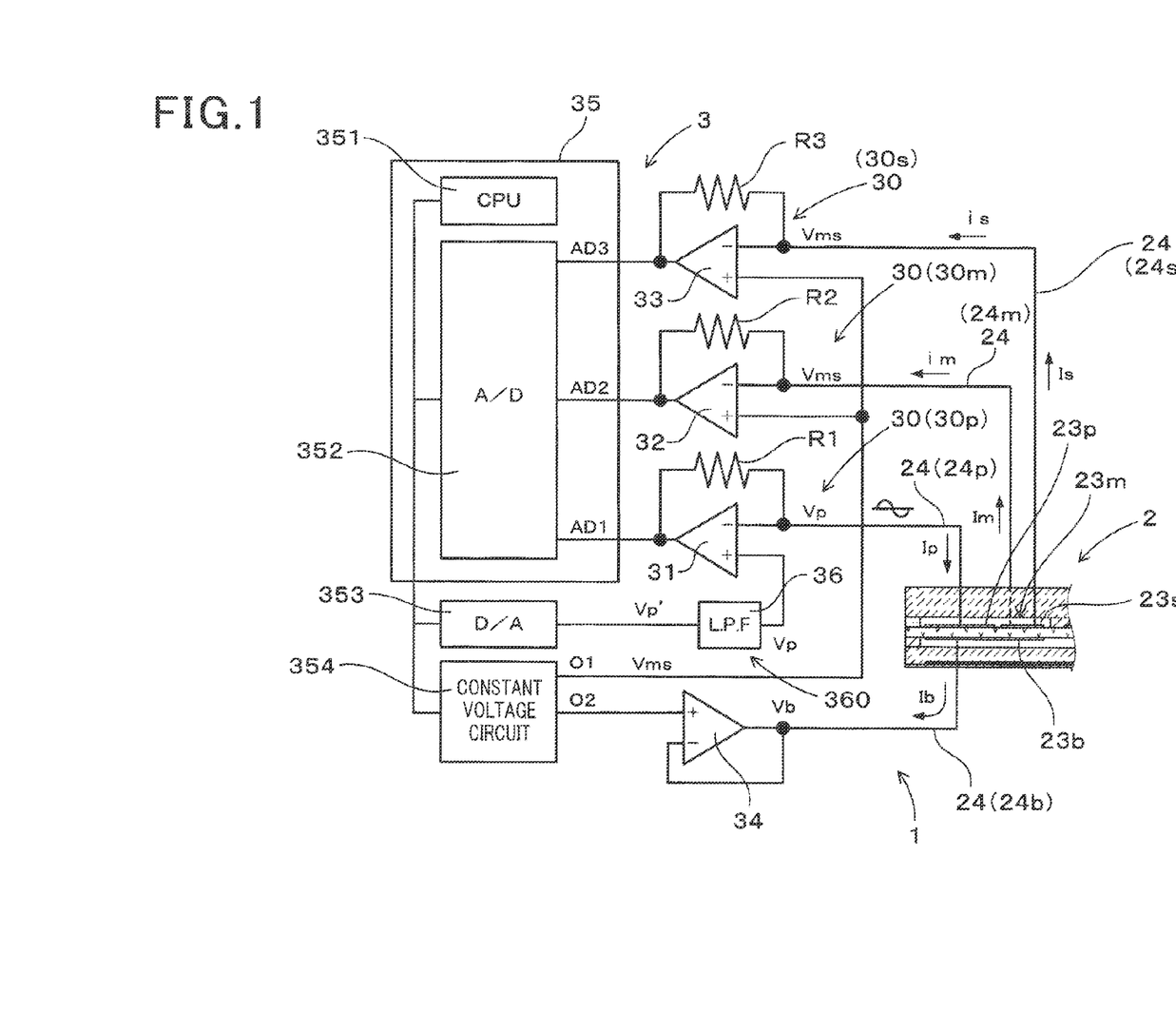
FIG. 1 is a diagram schematically showing the structure of a gas concentration detector according to an embodiment of the invention.

A gas concentration detector 1 according to an embodiment of the invention is described with reference to FIGS. 1 to 13. As shown in FIG. 1, the gas concentration detector 1 includes a gas sensor 2 end an abnormality detecting section 3 connected to the gas sensor 2.

As shown in FIGS. 2 to 6, the gas sensor 2 includes a solid electrolyte body 22 having oxygen ion conductivity, electrodes 23 formed on both surfaces of the solid electrolyte body 22, wires 24 each connected to a corresponding one of the electrodes 23 as a current passage. The electrodes 23 includes a pump electrode 23p, monitor electrode 23m and a sensor electrode 23s which are formed on one of the surfaces of the solid electrolyte body 22 so as to be exposed to a measurement gas g, and a reference electrode 23b formed on the other surface of the solid electrolyte body 22 so as to be exposed to a reference gas. The wires 24 include a pump wire 24p connected to the pump electrode 23p, a monitor wire 24m connected to the monitor electrode 23m, a sensor wire 24s connected to the sensor electrode 23s and a reference wire 24b connected to the reference electrode 23b.

Figure 2:
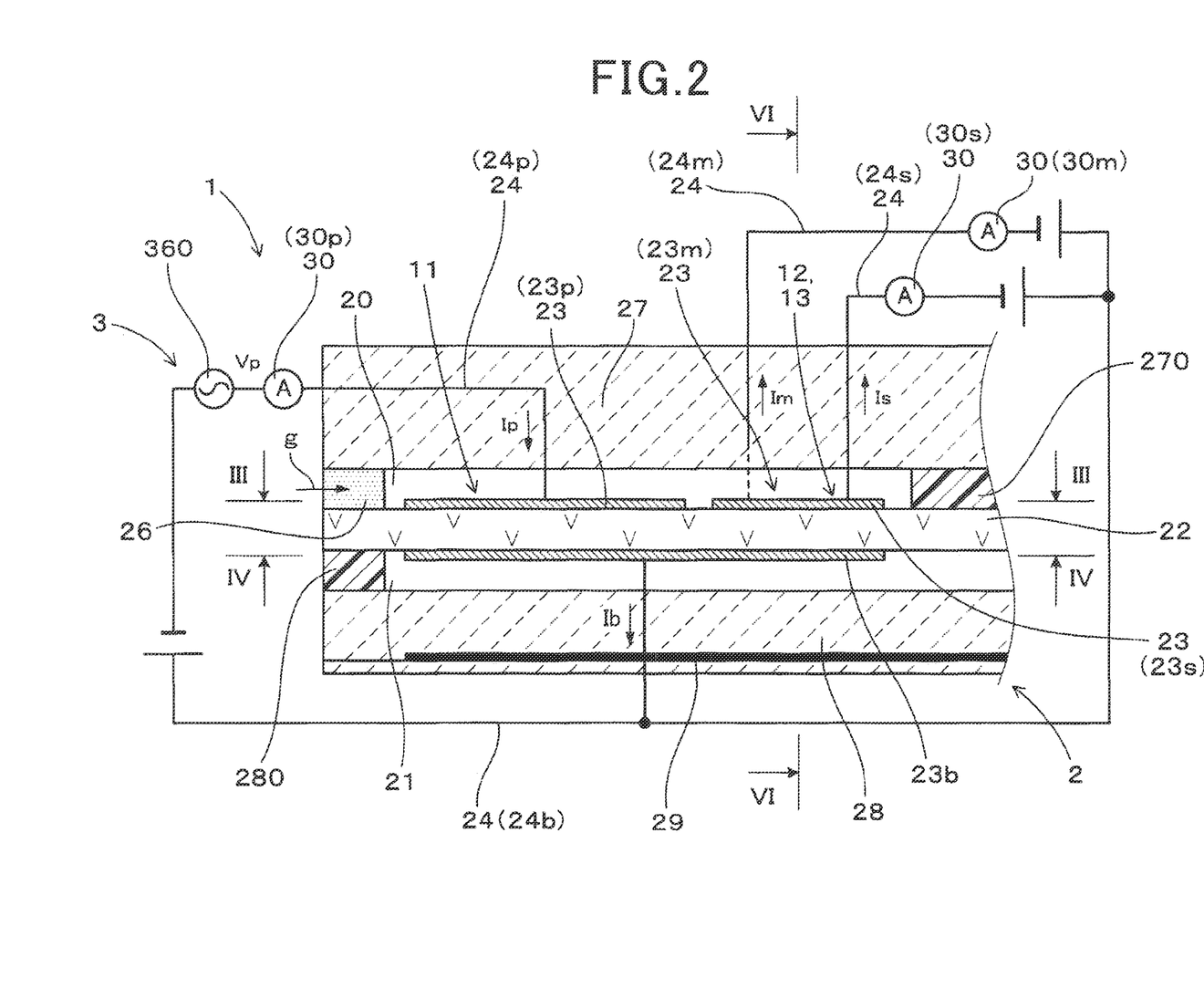
FIG. 2 is a diagram showing a partial cross-sectional view of a gas sensor included in the gas concentration detector together with the circuit diagram of its abnormality detecting section.

The solid electrolyte body 22, the pump cell 23p and the reference electrode 23 constitute a pump cell 11 for adjusting the oxygen concentration in the measurement gas. The solid electrolyte body 22, the monitor electrode 23m and the reference electrode 23b constitute a monitor cell 12 for measuring the oxygen concentration in the measurement gas. The solid electrolyte body 22, the sensor electrode 23s and the reference electrode 23b constitute a sensor cell 13 for measuring a specific gas contained in the measurement gas. The pump electrode 23p, the monitor electrode 23m, the sensor electrode 23s and the reference electrode 23b are formed in the single solid electrolyte body 22.

As shown in FIGS. 1 and 2, the pump cell 11, the monitor cell 12 and the sensor cell 13 are connected with current measuring sections 30p, 30m and 30s, respectively. The abnormality detecting section 3 applies an AC voltage to a specific one of the electrodes 23 (the pump electrode 23p in this embodiment) relative to the reference electrode 23b. At this time, the current measuring sections 30p, 30m and 30s measure a currents Ip flowing to the pump electrode 23p, a current Im flowing to the monitor electrode 23m and a current Is flowing to the sensor electrode 23s, respectively, using the current measuring sections 30p, 30m and 30s. The abnormality detecting section 3 determines that at least one of the wires 24 is broken if at least one of the currents Ip, Im and Is is smaller than a predetermined value.

In this embodiment, the gas sensor 2 is an NOx sensor for measuring NOx concentration in exhaust gas.

Figure 5:
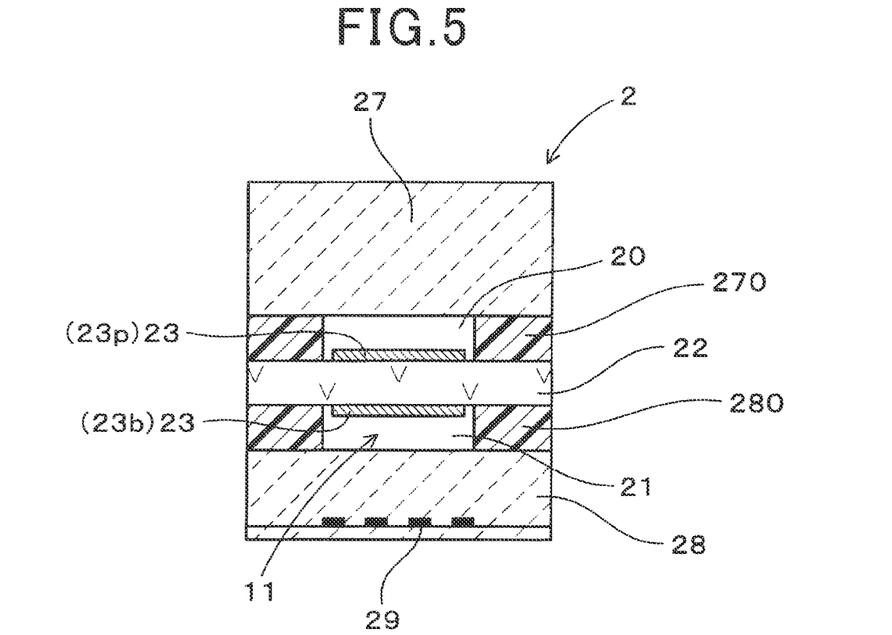
FIG. 5 is a cross-sectional view of FIG. 2 taken along line V-V.
Figure 6:
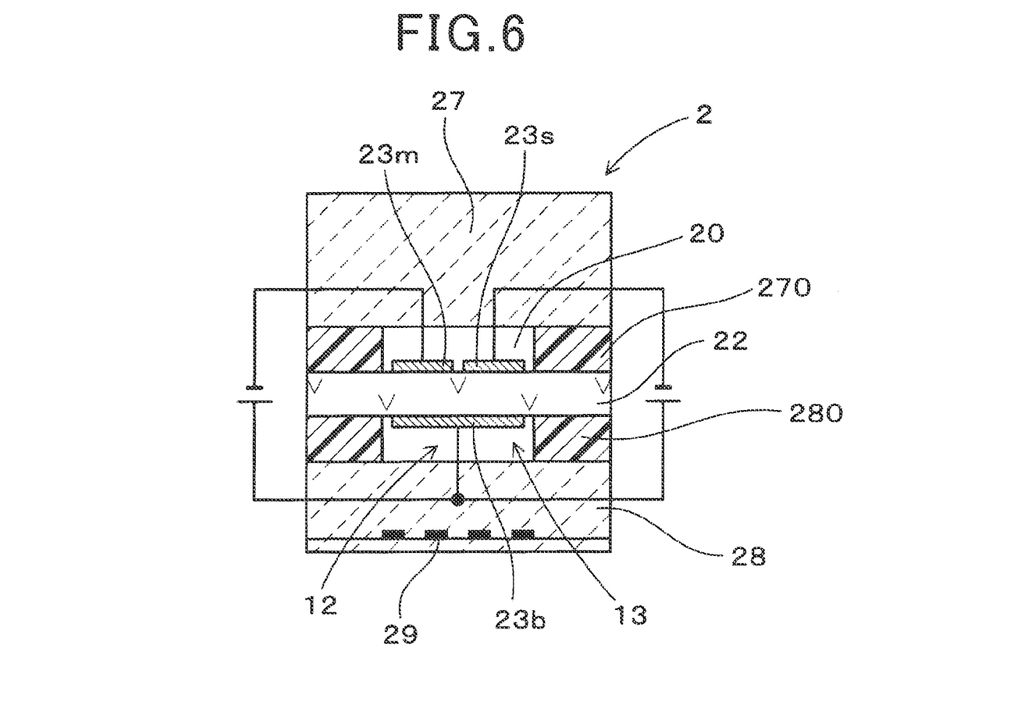
FIG. 6 is a cross-sectional view of FIG. 2 taken along line VI-VI.

As shown in FIGS. 2, 5 and 6, the gas sensor 2 includes a first insulating member 27 and a second insulating member 28. The solid electrolyte body 22 is made of zirconia. The first and second insulating members 27 and 28 are made of ceramic. Between the first insulating member 27 and the solid electrolyte body 22, a first space 27 is interposed to form a measurement gas chamber 20. Exhaust gas of an automobile is introduced as the measurement gas g into the measurement gas chamber 20. Between the second insulating member 28 and the solid electrolyte body 22, a second spacer 280 is interposed to form a reference gas chamber 21. The atmospheric air is introduced into the reference gas chamber 21 as the reference gas.

As shown in FIG. 2, the gas sensor 2 includes a diffused resistance section 26. The measurement gas g is introduced into the measurement gas chamber 20 through the diffused resistance section 26. The flow velocity of the measurement gas g is limited by the diffused resistance section 26.

The second insulating member 28 includes a heater 29 embedded therein. Prior to using the gas sensor 2, a current is supplied to the heater 29 to heat the solid electrolyte body 22 to a predetermined temperature.

Figure 3:
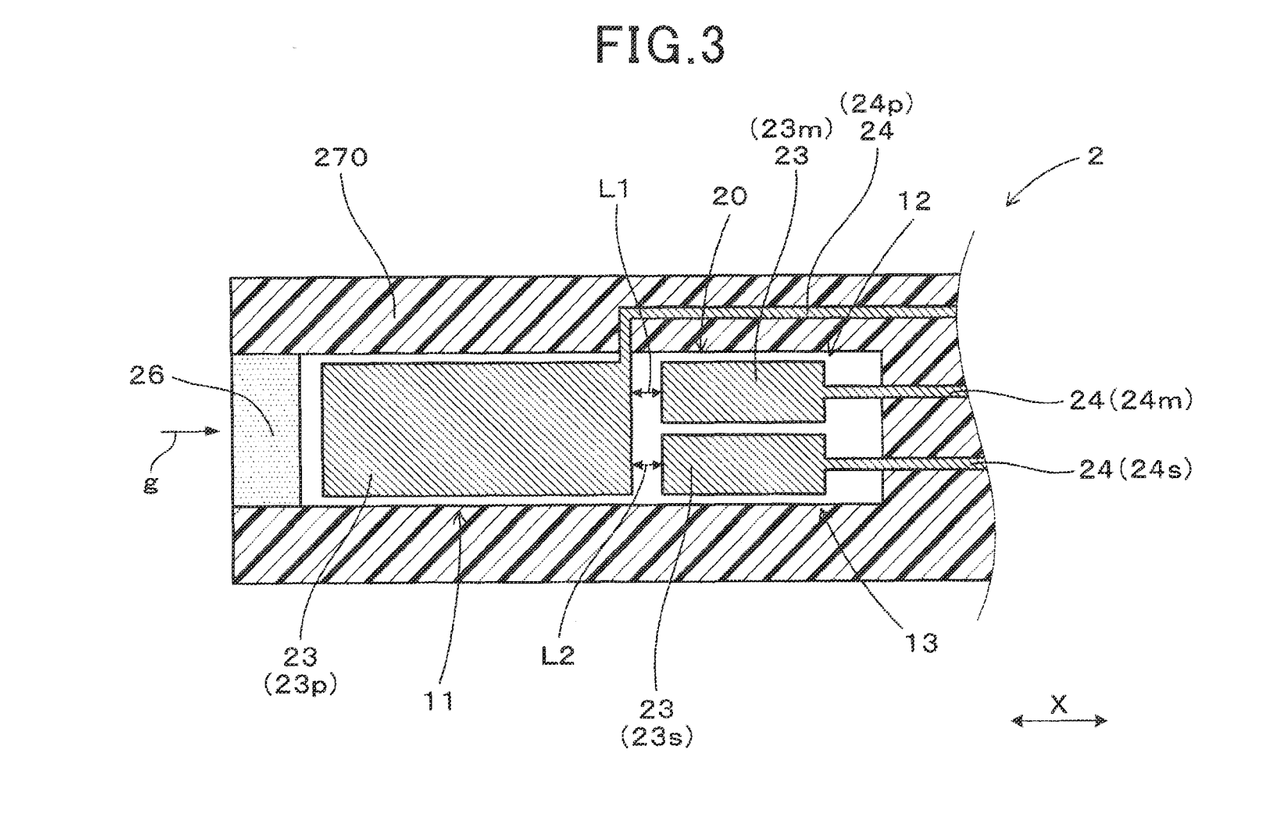
FIG. 3 is a cross-sectional view of FIG. 2 taken along line III-III.
Figure 4:
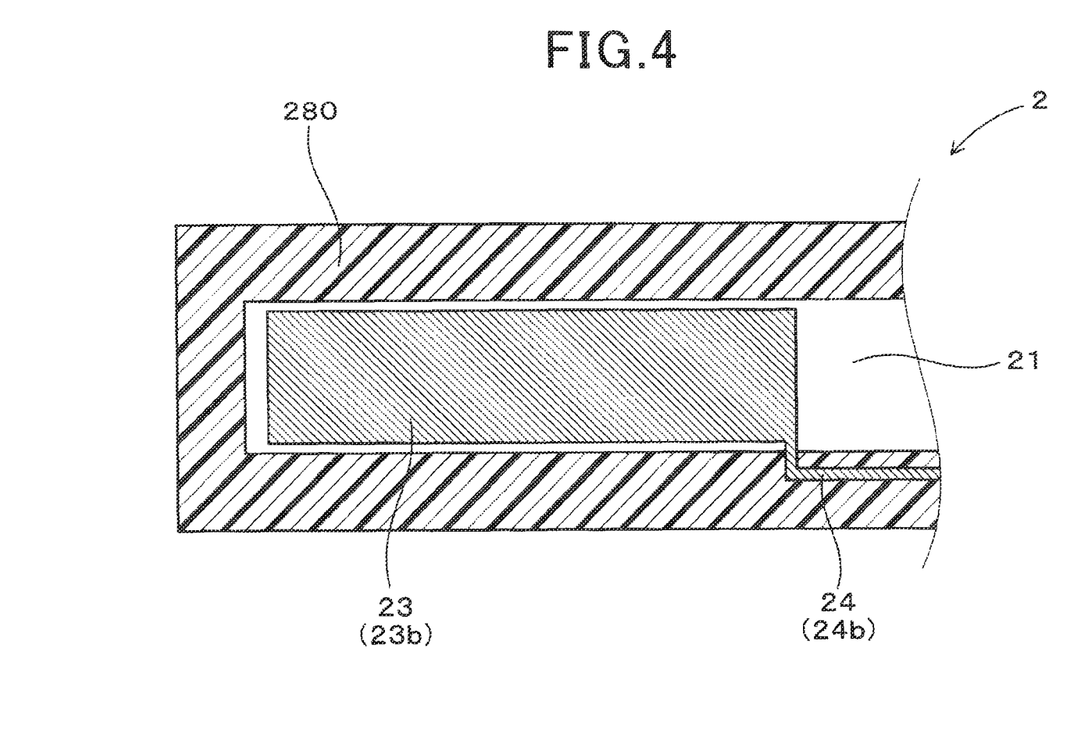
FIG. 4 is a cross-sectional view of FIG. 2 taken along line IV-IV.

As shown in FIGS. 3 and 4, each of the electrodes 23 has a rectangular shape. Each or the wires 24 is electrically connected to the abnormality detecting section 3 at its one end.

As shown in FIGS. 1 and 2, the pump wire 24p is connected with the pump current measuring section 30p for measuring the current flowing to the pump cell 11, the monitor wire 24m is connected with the monitor current measuring section 30m for measuring the current flowing to the monitor cell 12, and the sensor wire 24s is connected with the sensor current measuring section 30s for measuring the current flowing to the sensor cell 13.

The pump electrode 23p and the monitor electrode 23m are made of an alloy of Pt and Au. The sensor electrode 23s is made of an alloy of Pt and Ph. In this embodiment, to measure the concentration of the specific gas (NOx), a DC voltage is applied to each of the pump cell 11, the monitor cell 12 and the sensor cell 13 relative to the reference electrode 23b. More specifically, the reference electrode 23b is placed at a high potential, and the opposite electrodes (pump electrode 23p, monitor electrode 23m and sensor electrode 23s) are placed at a low potential.

When exhaust gas of an automobile is introduced into the measurement gas chamber 20, the oxygen molecules in the exhaust gas are decomposed into oxygen ions by the pump electrode 23p. The oxygen ions move through the solid electrolyte body 22 and are discharged to the reference gas chamber 21. As a result, the oxygen concentration of the exhaust gas is lowered.

A slight amount of oxygen molecules remain in the exhaust gas whose oxygen concentration has been lowered by the pump cell 11. The concentration of these oxygen molecules is measured using the monitor cell 12. That is, the oxygen molecules are decomposed into oxygen ions by the monitor electrode 23m, and the oxygen ions are discharged to the reference gas chamber 21 through the solid electrolyte body 22. The current flowing to the monitor cell 12 as this time is measured by the monitor current measuring section 30m. The remaining oxygen concentration A1 is calculated based on the value of the measured current.

In this embodiment, the concentrations of the oxygen molecules and NOx contained in the exhaust gas whose oxygen concentration has been reduced by the pump cell 11 are measured using the sensor cell 13. That is, the oxygen molecules and NOx are decomposed to produce oxygen ions by the sensor electrode 23s. The oxygen ions are discharged to the reference gas chamber 21 through the solid electrolyte body 22. At this time, the current flowing to the sensor cell 13 is measured by the sensor current measuring section 30s (see FIGS. 1 and 2). The concentration A2 of the sum of the oxygen molecules and NOx is calculated based on the value of the measured current. The concentration of NOx is calculated to be (A2−A1). These calculations are performed by a CPU 351 of a later-described microcomputer 35 (see FIG. 1).

Figure 7:
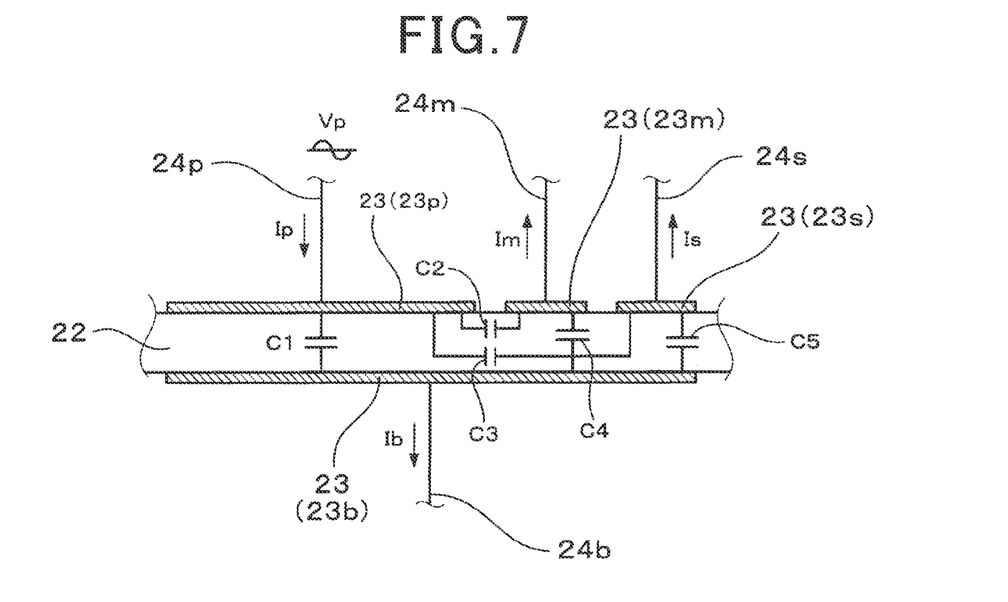
FIG. 7 is a diagram showing a schematic equivalent circuit of three cells included in the gas sensor.

As explained in the foregoing, the pump electrode 23p, the monitor electrodes 23m, the sensor electrode 23s and the reference electrode 23b are formed on the single solid electrolyte body 22. Accordingly, as shown in FIG. 7, a parasitic capacitance is present between each two of these electrodes 23. For example, a parasitic capacitance C1 is present between the pump electrode 23p and the reference electrode 23b, a parasitic capacitance C2 is present between the pump electrode 23p and the monitor electrode 23m, and a parasitic capacitance C3 is present between the pump electrode 23p and the sensor electrode 23s.

Accordingly, when the AV voltage Vp is applied to the pump electrode 23p, an AC current Ib flows between the pump electrode 23p and the reference electrode 23b through the solid electrolyte body 22, an AC current Im flows between the pump electrode 23p and the monitor electrode 23m through the solid electrolyte body 22, and an AC current Is flows between the pump electrode 23p and the sensor electrode 23 through the solid electrolyte body 22.

As shown in FIGS. 1 and 2, to perform wire breakage check, the AC voltage Vp is applied Vp to the pump electrode 23p through the pump wire 24p, and the AC currents Ip, Im and Is flowing respectively on the pump wire 24p, the monitor wire 24m and the sensor wire 24s in this state are measured by the current measuring sections 30p, 30m and 30s. If any one of the wires 24p, 24m, 24s and 24b is broken, one of the values of the AC currents Ip, Im and Is is measured to be smaller than its normal value. The abnormality detecting section 3 determines whether there is a wire breakage in the wires 24 based on the measured values of the AC currents Ip, Im and Is.

Figure 8:
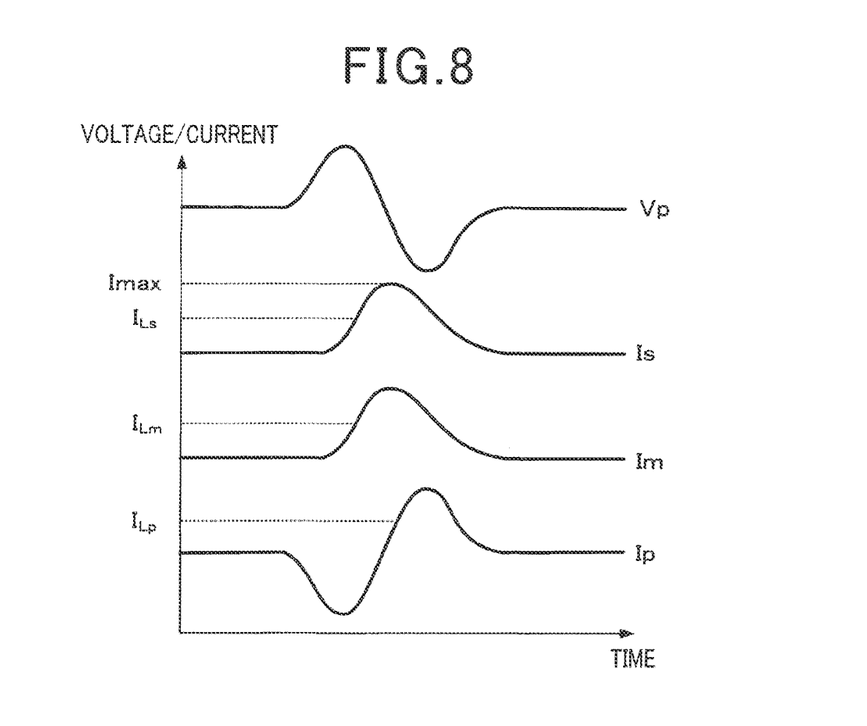
FIG. 8 is a graph showing temporal variations of an AC voltage applied to one of the cells and currents flowing on a sensor wire, a monitor wire and a pump wire, respectively when there is no wire breakage in the gas concentration detector.

When the AC voltage Vp is applied to the pump electrode 23p, the current measuring sections 30p, 30m and 30s detect the AC currents Ip, Im and Is respectively flowing on the wires 24p, 24m and 24s as shown in FIG. 8. For example, to determine whether or not the sensor wire 24s is broken, the abnormality detecting section 3 performs comparison between the maximum value Imax of the measured AC current Is with a predetermined reference value ILs. The abnormality detecting section 3 performs such comparisons also for the AC currents Ip and Im. If the maximum value has been detected to be larger than the reference value for all of the AC currents Is, Im and Ip, the abnormality detecting section 3 determines that none of the wires 24 is broken.

Figure 9:
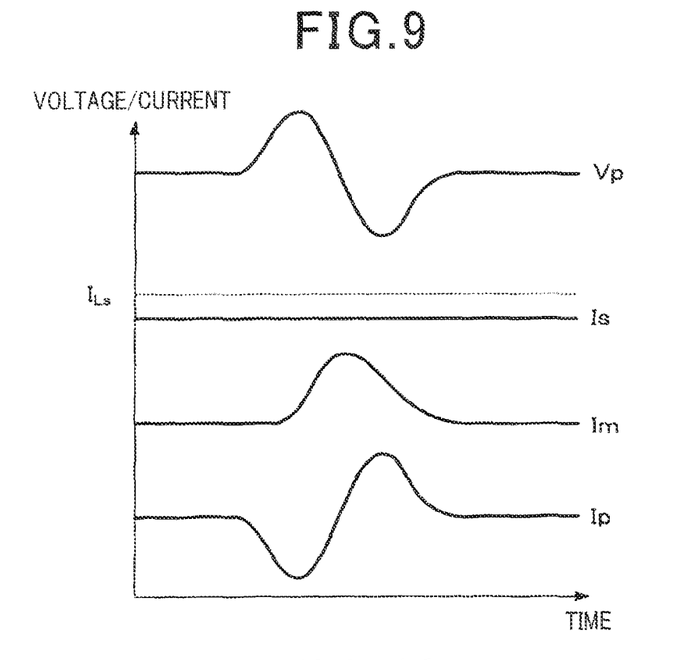
FIG. 9 is a graph showing temporal variations of the AC voltage applied and the currents when the sensor wire is broken.

In a case where the sensor wire 24s is broken, the value of the AC current Is measured by the sensor current measuring section 30s does not exceed the predetermined reference value ILs as shown in FIG. 9.

Figure 10:
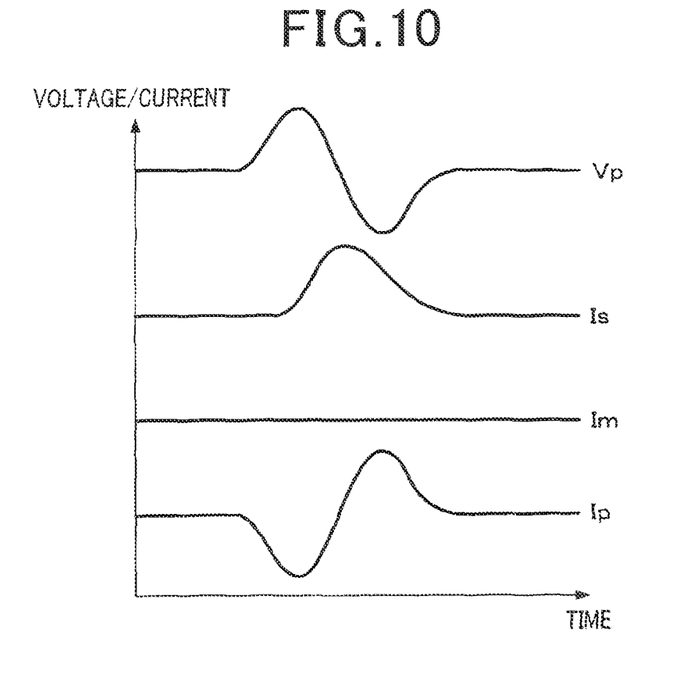
FIG. 10 is a graph showing temporal variations of the AC voltage applied and the currents when the monitor wire is broken.

In a case where the monitor wire 24m is broken, the value of the AC current Im measured by the monitor current measuring section 30m is null as shown in FIG. 10.

Figure 11:
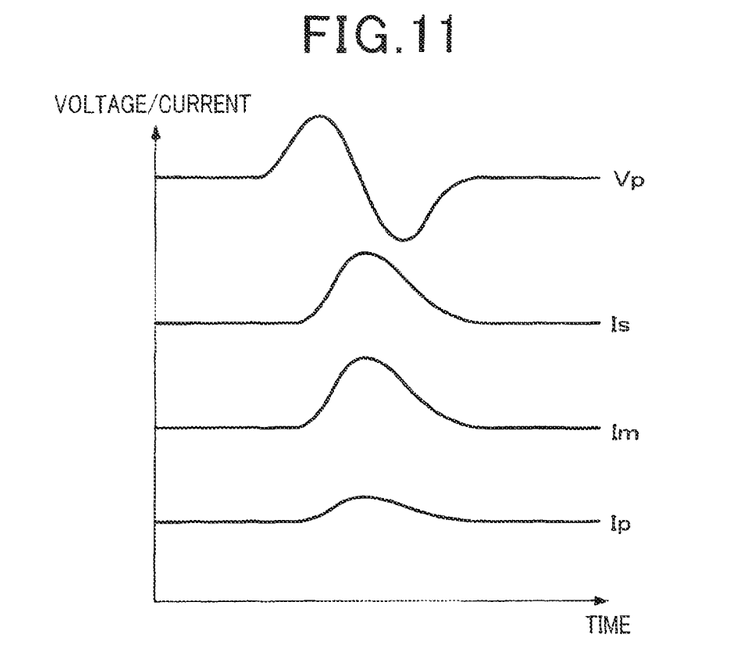
FIG. 11 is a graph showing temporal variations of the AC voltage applied and the currents when a reference wire is broken.

In a case where the reference wire 24b is broken, the waveforms of the AC currents Is, Im and Ip are as shown in FIG. 11. In this case, the AC current Is flowing between the pump electrode 23p and the sensor electrode 23s and the AC current flowing between the pump electrode 23p and the monitor electrode 23m are measured to be normal. Since the AC current Ib is null because the reference wire 24b is broken, the AC current IP is measured to be the sum of the AC currents Is and Im.

Figure 12:
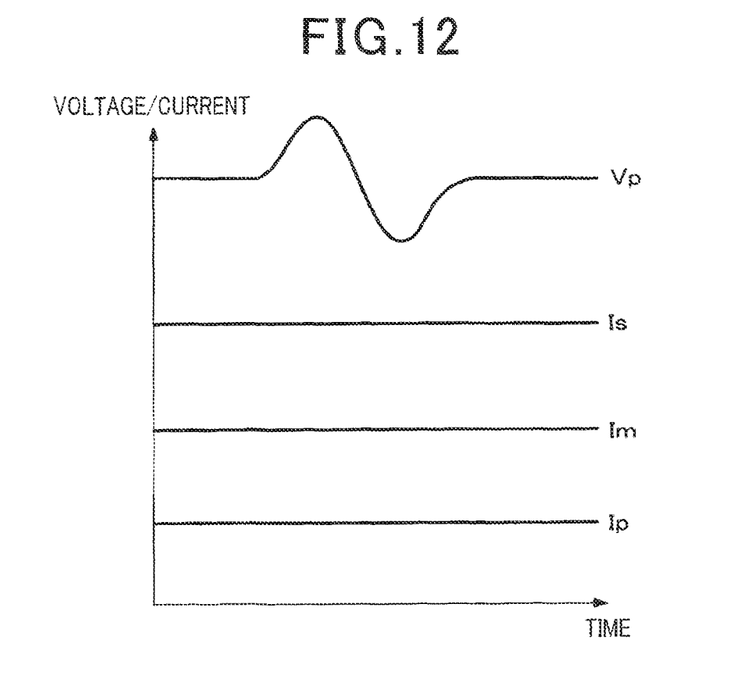
FIG. 12 is a graph showing temporal variations of the AC voltage applied and the currents when the pump wire is broken.

In a case where the pump wire 24p is broken, the waveforms of the AC currents Is, Im and Ip are as shown in FIG. 12. In this case, all of the AC currents Is, Im and Ip are null because no voltage is applied to the pump electrode 23p.

If the waveforms of the AC currents Is, Im and Ip are as shown in any one of FIGS. 9 to 12, the abnormality defecting section 3 determines that at least one of the wires 24p, 24m, 24s and 24b is broken.

Next, the circuit structure of the gas concentration detector 1 is explained. As shown in FIG. 1, the abnormality detecting section 3 includes the microcomputer 35, a D/A converter 353 and a constant voltage circuit 354. The microcomputer 35 doubles as a concentration calculator for calculating the NOx concentration of the exhaust gas. The microcomputer 35 includes therein a CPU 351 and an A/D converter 352.

The A/D converter 352 is connected with three operational amplifiers 31, 32 and 33. These operational amplifiers 31, 32 and 33 are used as the current measuring sections 30. The non-inverting input terminal of the first operational amplifier 31 is connected to the D/A converter 353 through a low-pass filter 36. The non-inverting input terminals of the second operational amplifier 32 and the third operational amplifier 33 are connected to the first output terminal O1 of the constant voltage circuit 354. The inverting input terminals of the operational amplifiers 31, 32 and 33 are connected to the pump wire 24p, the monitor wire 24m and the sensor wire 24s, respectively. Resistors R1, R2 and R3 are provided between the output terminals and the inverting input terminals of the operational amplifiers 31, 32 and 33, respectively.

The constant voltage circuit 354 is connected with a fourth operational amplifier 34 as a voltage follower. The output terminal of the fourth operational amplifier 34 is connected with the reference wire 24b. The output voltage Vb of the constant voltage circuit 354 is applied to the reference electrode 23b of the gas sensor 2 through the fourth operational amplifier 34.

To perform breakage check of the wires 24, the D/A converter 353 generates an AC voltage. This AC voltage is smoothed to have the waveform of the AC voltage shown in FIG. 8 by the low-pass filter 36.

As shown in FIG. 1, the AC voltage smoothed by the low-pass filter 36 is applied to the non-inverting input terminal of the first operational amplifier 31. At this time, the voltage of the non-inverting input terminal is substantially equal to the voltage of the inverting input terminal due to the virtual short-circuit therebetween. Accordingly, the pump electrode 230 is applied with the AC voltage Vp.

At this time, if none of the wires 24 is broken, an AC current flows on each of all the wires 24 as described in the foregoing. When then AC current Is flows on the sensor wire 24s, the voltage $V_{AD3}$ of the input terminal AD3 of the A/D converter 352 is detected to be Vms−Is·R3 where Vms is the voltage applied to the sensor electrode 23s. Since the voltage Vms is the output voltage of the first output terminal O1 of the constant voltage circuit 354, its value is known. The resistance of the resistor R3 is also known. Accordingly, by measuring the voltage $V_{AD3}$, the AC current Is can be determined. The other AC currents Im and Ip can be determined in a similar way.

Next, a method of measuring the NOx concentration of the exhaust gas is explained. To measure the NOx concentration, the constant voltage circuit 354 outputs a DC voltage Vms from its first output terminal O1. This DC voltage Vms is applied to the monitor electrode 23m and the sensor electrode 23s through the second operational amplifier 32 and the third operational amplifier 33. Further, the constant voltage circuit 345 outputs a DC voltage Vb from its second output terminal O2. This DC voltage Vb is applied to the reference electrode 23b. Further, the D/A converter 353 outputs a DC voltage Vp'. This DC voltage Vp' is applied to the pump electrode 23p through the low-pass filter 36 and the first operational amplifier 31.

A current im corresponding to the oxygen concentration of the exhaust gas whose oxygen concentration has been reduced by the pump cell 11 flows on the monitor wire 24. On the other hand, a current is corresponding to the concentration of the sum of oxygen and Nox contained in the exhaust gas flows on the sensor wire 24s. The values of these currents are measured by the current measuring sections 30m and 30s. The CPU 351 calculates the NOx concentration based on these measured values.

Figure 13:
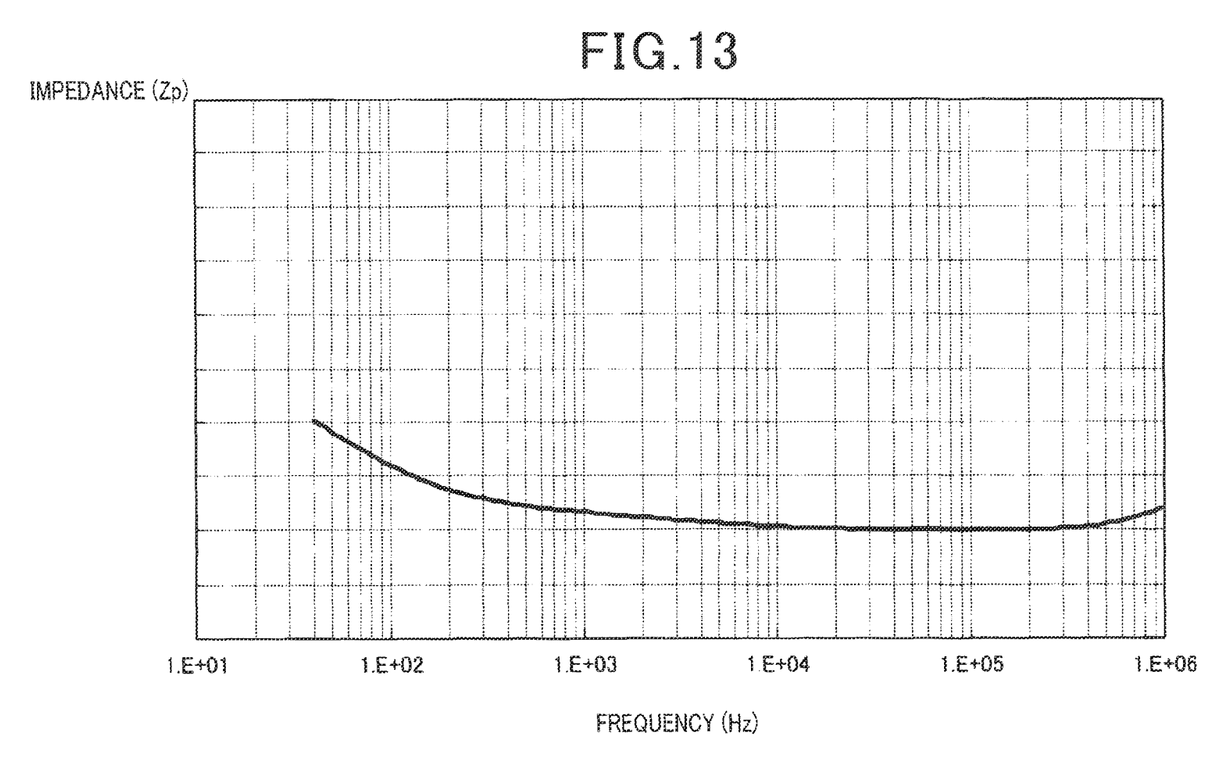
FIG. 13 is a graph showing a relationship between the frequency of the AC voltage and the impedance between a pump electrode and a reference electrode in the gas concentration detector according to the embodiment.

Next, a relationship between the frequency of the AC voltage Vp applied to the pump electrode 23p and the inter-electrode impedance is explained with reference to FIG. 13. The graph of FIG. 13 shows how the impedance Zp between the pump electrode 23p and the reference electrode 23b vanes when the frequency of the AC voltage Vp is changed in the range from 40 Hz to 106 Hz. The Impedance Zp is equal to the AC voltage Vp divided by the AC current Ip. That is, Zp=Vp/Ip As seen from the graph of FIG. 13, the impedance Zp does not vary much with the change of the frequency of the AC voltage Vp as long as the frequency of the AC voltage Vp is between 1 kHz and 300 kHz. To check breakage of the wires 24, it is preferable to measure the AC current Ip in a range where the impedance Zp does not vary much with the change of the frequency of the AC voltage Vp, so that the AC current Ip can be measured accurately. While on the other hand, when the frequency of the AC voltage Vp is too high, it is difficult for the current measuring section 30 to measure the AC current Ip accurately. Hence, it is preferable to set the frequency of the AC voltage Vp between 1 kHz and 50 kHz.

Incidentally, the impedance Zm between the pump electrode 23p and the monitor electrode 23 and the impedance Zs between the pump electrode 23p and the sensor electrode 23s have the similar frequency characteristic to the impedance Zp. Accordingly, it is preferable to set the frequency of the AC voltage Vp between 1 kHz and 50 kHz.

Next, advantages of the embodiment described above are explained. As shown in FIGS. 2 and 7, the pump electrode 23p, the monitor electrode 23m, the sensor electrode 23s and the reference electrode 23b are formed in the single solid electrolyte body 22. Accordingly, the solid electrolyte body 22 interposes between each two of these electrodes 23, and a parasitic capacitance is present between each two of these electrodes 23. Therefore, when an AC voltage is applied to any one of these electrodes 23, an AC current flows to each one of these electrodes 23 through the parasitic capacitance, and as a result, an AC current flows to each one of these electrodes 23. Hence, it is possible to check breakage of all the wires 24 only by applying an AC voltage to one of these electrodes 23. That is, it is not necessary to apply an AC voltage to each of the electrodes 23 individually to perform breakage check of the wires 24. This makes it possible to simplify the circuit structure of the abnormality detecting section 3 because the abnormality detecting section 3 requires only one AC voltage applying circuit 360 (see FIGS. 1 and 2). In addition, since the breakage check of the wires 24 can be done only by applying the AC voltage Vp to one of the electrodes 23 only once, the period of time necessary to complete the breakage check of the wires 24 can be made short.

This embodiment is configured to apply the AC voltage Vp to the pump electrode 23p to perform the wire breakage check. This enables accurately measuring the current im flowing to the monitor cell 12 and the current is flowing to the sensor cell 13 cell when the concentration of the specific gas is measured. This is because, since the D/A converter 353 and the low-pass filter 36 constituting the AC voltage applying circuit 360, which may become a source of error at the time of measuring a very small current, are necessary to apply the AC voltage Vp, it is preferable to avoid them from being connected to the cell to which a very small current flows. When the concentration of the specific gas is measured, a relatively larger current flows to the pump cell 11, while on the other hand, a very small current flow to the monitor cell 12 and the sensor cell 13. Accordingly, by mounting the AC voltage applying circuit 360 not to the monitor cell 12 or the sensor cell 13 but to the pump cell 11, it becomes possible to prevent the small currents im and is respectively flowing on the monitor cell 12 and sensor cell 13 from leaking greatly outside the AC voltage applying circuit 360, so that the measuring accuracy of the currents im and is can be improved.

In this embodiment, since the AC voltage Vp is applied to the pump electrode 23p, the structures of the current measuring sections 30p, 30m and 30s can be simplified. A large AC current flows to the cell applied with the AC voltage Vp at the time of performing the wire breakage check. Accordingly, in a case where the AC voltage Vp is applied to the monitor electrode 23m or the sensor electrode 23s, the very small currents im and is flow on the monitor wire 24m and the sensor wire 24s, respectively, at the time of measuring the concentration of the specific gas, while on the other hand, the large AC currents Im and Is flow on the monitor wire 24m and the sensor wire 24s, respectively, at the time of performing the wire breakage check. Accordingly, in this case, the current measuring sections 30s and 30m have to be provided with a switching circuit to enable measuring both the large and very small currents. In addition, since a current leaks from such a switching circuit, the defection accuracy may be worsened. In contrast, a large current flows on the pump wire 240 at the time of measuring the concentration of the specific gas. Accordingly, in the case where the AC voltage Vp is applied to the pump electrode 23p at the time of performing the wire breakage check, the value of a current flowing on the pump wire 24p at the time of measuring the concentration of the specific gas is roughly the same as the value of a current flowing on the pump wire 24p at the time of performing the wire breakage check. Hence, in this case, the structure of the pump current measuring section 30p can be simplified because it does not need a switching circuit.

In this embodiment, as shown in FIGS. 2 and 7, the reference electrode 23b is common to the pump cell 11, the monitor cell 12 and the sensor cell 13. Accordingly, the AC currents Im and Is flowing respectively on the monitor wire 24m and the sensor wire 24s while the wire breakage check is performed can be measured easily. If the reference electrode 23b is divided into three parts corresponding to the three cells 11 to 13, a parasitic capacitance is present between the pump electrode 23p and each of the three parts. Further, a parasitic capacitance is present between the sensor electrode 23m and each of the three parts, and between the sensor electrode 23s and each of the three parts. As a result, when the AC voltage VP is applied to the sump electrode 23p, since AC currents flow through various paths, the AC currents Im and Is flowing respectively on the monitor wire and the sensor wire may become too small. Hence, it is preferable that the reference electrode 23b is common to the pump cell 11, the monitor cell 12 and the sensor cell 13.

In this embodiment, as shown in FIG. 3, the measurement gas chamber 20 is not provided with any partition or aperture between the side of the pump electrode 23p and the side of the sensor electrode 23s and the monitor electrode 23p. Accordingly, since the measurement gas g floss smoothly from the side of the pump electrode 23p to the side of the sensor electrode 23s and the monitor electrode 23, it is possible to detect a change of the concentration of the specific gas contained in the measurement gas promptly. That is, the responsiveness of the gas sensor 2 can be made high.

In this embodiment, as shown in FIG. 3, the distance L1 between the pump electrode 23p and the monitor electrode 23m and the distance L2 between the pump electrode 23p and the sensor electrode 23s in the flow direction of the measurement gas g (in the X-direction) are equal to each other. Accordingly, the measurement gas g whose oxygen concentration has been reduced after passing over the pump electrode 23p reaches the monitor electrode 23m and the sensor electrode 23s approximately at the same time. That is, since the oxygen concentration of the measurement gas g at the monitor electrode 23m is almost the same as that at the sensor electrode 23s, the concentration of the specific gas can be calculated with a high degree of accuracy.

As described above, according to the embodiment of the invention, there is provided a gas concentration detector having an abnormality detecting section being simple in structure, and capable of determining whether there is a wire breakage in a short time.

In the above embodiment, the AC voltage is applied to the pump electrode 23p. However, the AC voltage may be applied to the reference electrode 23b or the monitor electrode 23m or the sensor electrode 23s.

In the above embodiment, the D/A converter 353 and the constant voltage circuit 354 are provided separately from the microcomputer 35. However, they may be incorporated in the microcomputer 35.

The above explained preferred embodiments are exemplary of the invention of the present application which is described solely by the claims appended below. It should be understood that modifications of the preferred embodiments may be made as would occur to one of skill in the art.

What is claimed is:

1. A gas concentration detector comprising a gas sensor and an abnormality detecting section connected to the gas sensor for detecting abnormality in the gas sensor,
    wherein
    the gas sensor includes a solid electrolyte body having oxygen ion conductivity, electrodes formed on both surfaces of the solid electrolyte body, and wires respectively connected to the electrodes,
    the electrodes include a pump electrode, a monitor electrode and a sensor electrode which are formed on one of the surfaces of the solid electrolyte body so as to be exposed to a measurement gas, and a reference electrode formed on the other surface of the solid electrolyte body so as to be exposed to a reference gas,
    the solid electrolyte body, the pump electrode and the reference electrode form a pump cell for adjusting an oxygen concentration of the measurement gas,
    the solid electrolyte body, the monitor electrode and the reference electrode form a monitor cell for detecting the oxygen concentration of the measurement gas,
    the solid electrolyte body, the sensor electrode and the reference electrode form a sensor cell for detecting a concentration of a specific gas contained in the measurement gas,
    the pump electrode, the monitor electrode, the sensor electrode and the reference electrode are formed in the solid electrolyte body,
    each of the wires respectively connected to the pump electrode, the monitor electrode and the sensor electrode are connected with a current measuring section,
    the abnormality detecting section is configured to apply an AC voltage to a specific one of the pump electrode, the monitor electrode, the sensor electrode and the reference electrode, and concurrently measure currents flowing respectively at a same time between the specific one of the pump electrode, the monitor electrode, the sensor electrode and the reference electrode and each of the other of the pump electrode, the monitor electrode, the sensor electrode and the reference electrode through the solid electrolyte body using the current measuring section, and the abnormality detecting section is configured to determine that at least one of the wires respectively connected to the pump electrode, the monitor electrode, the sensor electrode and the reference electrode is broken if at least one of the currents measured by the current measuring section is smaller than a predetermined value.

2. The gas concentration detector according to claim 1, wherein the abnormality defecting section is configured to apply the AC voltage to the pump electrode relative to the reference electrode.

3. The gas concentration detector according to claim 1, wherein the reference electrode is common to the pump cell, the monitor cell and the sensor cell.

* * * * *